United States Patent [19]

Cereda et al.

[11] Patent Number: 4,666,932
[45] Date of Patent: May 19, 1987

[54] FORMAMIDINE DERIVATIVES AND PHARMACEUTICAL USE

[75] Inventors: Enzo Cereda, Tortona; Giuseppe Bietti, Milan; Arturo Donetti, Milan; Piero del Soldato, Monza; Antonio Giachetti, Milan; Ferdinando Pagani, Verano Brianza, all of Italy

[73] Assignee: Istituto de Angeli S.p.A., Milan, Italy

[21] Appl. No.: 751,081

[22] Filed: Jul. 2, 1985

Related U.S. Application Data

[63] Continuation-in-part of Ser. No. 491,367, May 4, 1983, abandoned.

[30] Foreign Application Priority Data

May 18, 1982 [IT] Italy .................. 21331 A/82

[51] Int. Cl.$^4$ .................. A61K 31/415; C07D 233/64
[52] U.S. Cl. .................. 514/400; 514/397; 548/336; 548/346
[58] Field of Search .................. 548/336, 346; 514/397, 514/400

[56] References Cited

U.S. PATENT DOCUMENTS 4,386,099  5/1983  Cereda et al. .................. 548/336 X
4,438,127  3/1984  Durant et al. .................. 548/136 X

FOREIGN PATENT DOCUMENTS 1296544  11/1972  United Kingdom .

Primary Examiner—Richard L. Raymond
Attorney, Agent, or Firm—Hammond & Littell, Weissenberger & Dippert

[57] ABSTRACT

Compounds of the formula

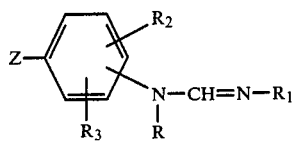

wherein
R is hydrogen or methyl;
$R_1$ is straight or branched alkyl of 1 to 6 carbon atoms, dimethyldioxolylmethyl, hydroxymethyldioxolylmethyl, hydroxy(alkyl of 1 to 6 carbon atoms), mono- or di-(alkoxy of 1 to 6 carbon atoms)(alkyl of 1 to 6 carbon atoms), (alkyl of 1 to 6 carbon atoms)thio-(alkyl of 1 to 6 carbon atoms), (alkoxy of 1 to 6 carbon atoms)(alkyl of 1 to 6 carbon atoms)thio-(alkyl of 1 to 6 carbon atoms), cyano(alkyl of 1 to 6 carbon atoms), di-lower alkyl-amino(alkyl of 1 to 6 carbon atoms), alkenyl, alkynyl, or cycloalkyl;
$R_2$ and $R_3$ are each independently hydrogen, alkyl of 1 to 3 carbon atoms, alkoxy of 1 to 3 carbon atoms or halogen; and
Z is imidazol-2-yl or imidazol-4-yl;
provided however, that, when $R_1$ is straight or branched alkyl, alkenyl, alkynyl, cycloalkyl or cyano and R, $R_2$ and $R_3$ are hydrogen, Z is other than imidazol-4-yl; tautomers thereof and non-toxic, pharmacologically acceptable acid addition salts thereof. The compounds as well as their salts are useful as antiulcerogenics and gastric acid secretion inhibitors.

13 Claims, No Drawings

FORMAMIDINE DERIVATIVES AND PHARMACEUTICAL USE

This is a continuation-in-part of copending application Ser. No. 491,367, filed May 4, 1983, now abandoned.

This invention relates to novel formamidine derivatives and acid addition salts thereof, to methods of preparing these compounds, to pharmaceutical compositions containing them as active ingredients, and to methods of using them as gastric acid secretion inhibitors and antiulcerogenics.

BACKGROUND OF THE INVENTION AND THE PRIOR ART

It is known that classic antihistamines, such as mepyramine, are capable of antagonizing some effects of histamine mediated by $H_1$-receptors. However, these compounds have no effect on gastric acid secretion which is instead affected by other antihistaminic agents defined by Black et al. (Nature 236, 385, 1972) as histamine $H_2$-receptor antagonists. This has indicated that another kind of receptors ($H_2$) already described by Ash and Schild (Brit. J. Pharmacol. Chem. Ther. 1966, 27, 427–39), is involved in the gastric secretory response which is not blocked by the conventional antihistamines of the $H_1$-type.

Examples of $H_2$-receptor antagonists capable of antagonizing gastric acid secretion include burimamide, metiamide, and cimetidine. More recently, new $H_2$-antagonists, such as ranitidine (Bradshaw et al., Brit. J. Pharmacol. 66, 464P, 1979), tiotidine (P. O. Jellin, Life Sci. 25, 2001, 1979) and BL 6341 (Cavanagh et al., Fed. Proc., 40, 2652, 1981) have been discovered. These compounds are effective $H_2$-blockers capable of antagonizing gastric acid secretion to a greater extent than cimetidine and congeners. In copending U.S. application Ser. No. 465,572, filed Feb. 10, 1983, now U.S. Pat. No. 4,548,944, and U.S. Pat. No. 4,386,099 we have described new classes of histamine $H_2$-antagonists, namely imidazolyl-phenylamidines and guanidino-heterocyclylphenylamidines, which are potent $H_2$-blockers and active antagonists of gastric acid secretion. These compounds do not resemble the so far known $H_2$-antagonists, such as cimetidine, ranitidine, etc., and are characterized by a phenylformamidine grouping bearing variously substituted imidazolyl- and guanidino-heterocyclyl rings.

DESCRIPTION OF THE INVENTION

More particularly, the present invention relates to a novel class of formamidine derivatives represented by the formula

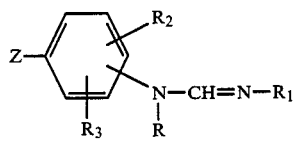 (I)

wherein
R is hydrogen or methyl;
$R_1$ is straight or branched alkyl of 1 to 6 carbon atoms, dimethyldioxolylmethyl, hydroxymethyldioxolylmethyl, hydroxy(alkyl of 1 to 6 carbon atoms), mono- or di-(alkoxy of 1 to 6 carbon atoms) (alkyl of 1 to 6 carbon atoms), (alkyl of 1 to 6 carbon atoms)thio(alkyl of 1 to 6 carbon atoms), (alkoxy of 1 to 6 carbon atoms) (alkyl of 1 to 6 carbon atoms)thio(alkyl of 1 to 6 carbon atoms), cyano(alkyl of 1 to 6 carbon atoms), di-lower alkyl-amino(alkyl of 1 to 6 carbon atoms), alkenyl, alkynyl or cycloalkyl;
$R_2$ and $R_3$ are each independently hydrogen, alkyl of 1 to 3 carbon atoms, alkoxy of 1 to 3 carbon atoms or halogen; and
Z is imidazol-2-yl or imidazol-4-yl;
provided however that, when $R_1$ is straight or branched alkyl, alkenyl, alkynyl, cycloalkyl or cyano, and R, $R_2$ and $R_3$ are hydrogen, Z is other than imidazol-4-yl; a tautomer thereof, or a non-toxic, pharmacologically acceptable acid addition salt thereof.

It is to be understood that, although the double bond in the formamidine radical has been inserted in a particular position, other tautomeric forms are possible when R is hydrogen, and that in the imidazole ring different tautomeric forms are also possible. The present invention includes such tautomeric forms within its scope, both in terms of the compounds of the invention and in terms of the methods of preparation.

More particularly, when $R_1$ is hydroxy(alkyl of 1 to 6 carbon atoms) it may be hydroxypropyl or hydroxybutyl; when $R_1$ is mono- or di-(alkoxy of 1 to 6 carbon atoms) (alkyl of 1 to 6 carbon atoms) it may be mono- or dimethoxyethyl or methoxypropyl; when $R_1$ is (alkyl of 1 to 6 carbon atoms)thio(alkyl of 1 to 6 carbon atoms) it may be methylthioethyl or ethylthioethyl; when $R_1$ is (alkoxy of 1 to 6 carbon atoms) (alkyl of 1 to 6 carbon atoms)thio(alkyl of 1 to 6 carbon atoms) it may be ethoxymethylthioethyl; when $R_1$ is cyano(alkyl of 1 to 6 carbon atoms) it may be cyanoethyl; when $R_1$ is dilower alkyl-amino(alkyl of 1 to 6 carbon atoms) it may be dimethylaminopropyl; when $R_1$ is alkenyl it may be alkenyl of 3 to 5 carbon atoms; when $R_1$ is alkynyl it may be alkynyl of 3 to 4 carbon atoms; when $R_1$ is cycloalkyl it may be cycloalkyl of 3 to 6 carbon atoms; and when $R_2$ and/or $R_3$ are halogen they may be bromine, chlorine, or fluorine.

In formula I the formamidine radical may be in the ortho-, meta- or para-position of the benzene ring with respect to Z, and substituents $R_2$ and/or $R_3$ may be in any position on the benzene ring.

Preferred compounds according to the present invention include those wherein the formamidine radical is in the paraposition with respect to the imidazolyl substituent; R represents a hydrogen atom; $R_1$ is propyl, isopropyl, butyl, sec.butyl, isobutyl, neopentyl, allyl, methoxyethyl, dimethoxyethyl, hydroxypropyl, hydroxybutyl, methylthioethyl, ethylthioethyl, cyanoethyl or ethoxymethylthioethyl, $R_2$ and/or $R_3$ represent hydrogen atoms, a methyl or methoxy group, or a bromine, chlorine or fluorine atom; and Z is imidazol-4-yl; and their non-toxic, pharmacologically acceptable acid addition salts.

Such compounds generally have better activity and are therefore preferred as antisecretory-antiulcer agents and for the treatment of disorders of the gastrointestinal tract.

The compounds of the formula I may, for example, be prepared by the following method:

Reaction of an N,N'-disubstituted formamidine of the formula:

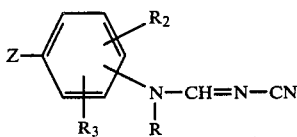

wherein Z, R, R₂ and R₃ have the meanings previously defined, with an amine of the formula

wherein R₁ has the meanings previously defined.

The reaction may conveniently be performed in the presence of water or of an inert aqueous organic solvent, for example in a lower alkanol such as methanol or ethanol, formamide, dimethylformamide, dioxane or acetonitrile. The reaction is generally carried out at a temperature from 10° to 50° C., preferably at room temperature.

The compounds of the formula II used as starting material in this method may be prepared by methods which are described in the literature, for example, by reacting an amine of the formula

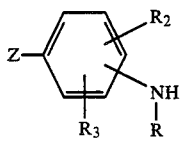

wherein Z, R, R₂ and R₃ have the meanings previously defined, with an N-cyano-alkylimidate of the formula

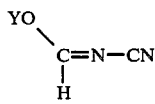

in which Y is lower alkyl, such as methyl or ethyl. The reaction may generally be carried out in the presence of a suitable inert organic solvent, such as a lower alkanol, an ether, ethylacetate, acetonitrile or dioxane, or also without solvent, at a temperature from 20° to 80° C., preferably at room temperature.

Optionally, the compounds of the formula II may be prepared in a single step by reacting an amine of the formula IV with cyanamide in the presence of a compound of the formula

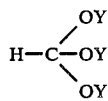

in which Y has the meaning previously defined. The reaction is carried out at a temperature of 50° to 150° C.

The compounds of the formula I prepared according to the above method may optionally be converted with inorganic or organic acids into non-toxic, pharmacologically acceptable acid addition salts, for example by conventional methods such as by reacting the compounds as bases with a solution of the corresponding acid in a suitable solvent, or by adding the acid solution directly to the reaction mixture obtained in the method without isolation of the compound as a base.

Particularly preferred acids include for example hydrochloric, sulfuric, maleic and fumaric acid. The compounds of the formula I and their non-toxic, pharmacologically acceptable acid addition salts are H₂-receptor blocking agents which inhibit gastric acid secretion.

Particularly preferred compounds of the present invention are the following:

N-(2-Methoxy ethyl)-N'-[4-(imidazol-4-yl)-phenyl]-formamidine,

N-(2-Hydroxy propyl)-N'-[4-(imidazol-4-yl)-phenyl]-formamidine,

N-(2-Methyl thio ethyl)-N'-[4-(imidazol-4-yl)-phenyl]-formamidine,

N-(2-Ethoxymethyl thio ethyl)-N'-[4-(imidazol-4-yl)-phenyl]-formamidine,

N-(2-Cyano ethyl)-N'-[4-(imidazol-4-yl)-phenyl]-formamidine,

N-n-Butyl-N'-[4-(imidazol-4-yl)-2-methyl-phenyl]-formamidine,

N-Allyl-N'-[4-(imidazol-4-yl)-2-methyl phenyl]-formamidine,

N-Propyl-N'-[4-(imidazol-4-yl)-2-methoxy-phenyl]-formamidine, and

N-Propyl-N'-[4-(imidazol-4-yl)-2-bromo-phenyl]-formamidine.

The following examples illustrate the present invention and will enable others skilled in the art to understand it more completely. It should be understood, however, that the invention is not limited solely to the particular examples given below.

PREPARATION OF STARTING COMPOUNDS

Example 1

4-(3-Methyl-4-aminophenyl)-1-H-imidazole (a) 4-(3-Methylphenyl)-1-H-imidazole nitrate (31 g) was added portionwise to concentrated sulfuric acid (78 ml) at room temperature. Then, the solution was heated at 90° C. for one hour and cooled. First water (200 ml) and then a 17% Na₂CO₃ solution was added until the pH was 7.5. The brown solid was filtered off and discarded. The solution was made strongly basic with 10% NaOH, and the yellow solid was filtered off and dried to give 9.5 g of 4-(3-methyl-4-nitrophenyl-1-H-imidazole, M.p. 138°-140° C. 4-(3-Methoxy-4-nitrophenyl)-1-H-imidazole, M.p. 171°-173° C., was prepared analogously.

(b) 4-(3-Methyl-4-nitrophenyl)-1-H-imidazole (9.2 g) was allowed to react with 85% hydrazine hydrate in methanol to give 7.9 g of 4-(3-methyl-4-aminophenyl)-1-H-imidazole, M.p. 195°-197° C. 4-(3-Methoxy-4-aminophenyl)-1-H-imidazole, M.p. 145° C. (dec.), was prepared analogously.

Example 2

N-Methyl-N-[4-(imidazol-4-yl)-phenyl]-amine (a) A solution of 4-(4-aminophenyl)-1-H-imidazole (10 g) in formic acid (100 ml) was refluxed for 4 hours and evaporated to dryness. The residue was dissolved in water, and the solution was filtered through charcoal and made basic to give 10 g of N-[4-(imidazol-4-yl)-phenyl]-formamide, M.p. 108°-109° C.

(b) A suspension of N-[4-(imidazol-4-yl)-phenyl]-formamide (8 g) in anhydrous tetrahydrofuran (80 ml) was slowly added dropwise to a suspension of LiAlH₄ (6.5 g) in anhydrous tetrahydrofuran. The reaction mixture was refluxed for 4 hours and cooled. Wet diethylether was added, and then the solution was evaporated to dryness. The residue was dissolved in water and ethylacetate. After working up the organic layer, 4.6 g of N-methyl-N-[4-(imidazol-4-yl)-phenyl]-amine, M.p. 75°–76° C., were obtained.

Example 3

4-[(3-bromo-4-amino)-phenyl]-1-H-imidazole (a) A solution of N-[2-bromo-4-(bromo-acetyl)-phenyl]-acetamide (4.6 g) in formamide (7.7 g) and water (0.9 ml) was heated at 140° C. for 4 hours. 10% Hydrochloric acid was added to the cold mixture, and the resulting solution was washed with ethyl acetate and then neutralized with 10% NaOH. The solid which crystallized out was filtered off and dried to give 2.2 g of 4-[(3-bromo-4-acetamido)-phenyl]-1-H-imidazole, M.p. 215°–217° C.

(b) A solution of 4-[(3-bromo-4-acetamido)-phenyl]-1-H-imidazole (1.8 g) in 6N hydrochloric acid (7.5 ml) was heated at 80° C. for 20 minutes and then neutralized with 10% NaOH. The oily product which separated out was extracted with ethyl acetate, and the extract was washed and evaporated to dryness to give 1.5 g of 4-[(3-bromo-4-amino)-phenyl]-1-H-imidazole as a thick reddish oil.

In analogous manner, starting from the appropriate intermediates, the following imidazole derivatives were also synthesized:
4-[(3-chloro-4-amino)-phenyl]-1-H-imidazole. Yellow oil.
4-[(3,5-dichloro-4-amino)-phenyl]-1-H-imidazole. M.p. 95°–98° C.
4-[3-chloro-5-bromo-4-amino)-phenyl]-1-H-imidazole. Brown oil.

Example 4

N-Cyano-N'-[2-methyl-4-(imidazol-4-yl)-phenyl]-formamidine

A solution of 4-(3-Methyl-4-amino-phenyl)-1-H-imidazole (15.9 g) and N-Cyano-ethylformimidate (9 g) in ethanol (100 ml) was stirred overnight at room temperature. The solid which crystallized out was filtered off and dried to give 11.3 of the desired compound. M.p. 200°–202° C.

By utilizing the above procedure, the following compounds were also prepared:
N-Cyano-N'-[4-(imidazol-4-yl)-2-bromo-phenyl]-formamidine, M.p. 183°–185° C.,
N-Cyano-N'-methyl-N'-[4-(imidazol-4-yl)-phenyl]-formamidine, M.p. 238°–239° C.,
N-Cyano-N'-[4-(imidazol-4-yl)-2-chloro-phenyl]-formamidine, M.p. 170°–171° C.,
N-Cyano-N'-(4-(imidazol-4-yl)-2,6-dichloro-phenyl]-formamidine, M.p. 158°–160° C.,
N-Cyano-N'-[4-(imidazol-4-yl)-2-chloro-6-bromo-phenyl]-formamidine, M.p. 178°–179° C.,
N-Cyano-N'-[4-(imidazol-4-yl)-2-methoxy-phenyl]-formamidine, M.p. 112°–116° C.

Example 5

N-Cyano-N'-[4-(imidazol-2-yl)-phenyl]-formamidine

A mixture of 2-(4-amino-phenyl)-1-H-imidazole (3.1 g), cyanamide (0.8 g) and triethyl orthoformate (3.6 g) was heated at 150° C. for a few minutes. The product which crystallized out was filtered off, washed with ethanol and dried to give 2.5 g of the title compound, M.p. 228°–229° C.

The following compound was prepared in analogous manner:
N-Cyano-N'-[3-(imidazol-2-yl)-phenyl]-formamidine, M.p. 202°–203° C.

PREPARATION OF END PRODUCTS OF THE FORMULA I

Example 6

N-(2-Methoxy-ethyl)-N'-[4-(imidazol-4-yl)-phenyl]-formamidine 5 ml of 2-methoxy-ethylamine were added all at once to a suspension of N-cyano-N'-[4-(imidazol-4-yl)-phenyl]-formamidine (1.8 g) in water (2 ml). When the exothermic reaction subsided, a solution was obtained from which the title compound quickly crystallized out. The product was filtered off and purified via its maleate in acetone.

Yield: 2.8 g, M.p. 146°–149° C. (dec.).
Analysis: $C_{21}H_{24}N_4O_9$: Found %: C-52.60; H-5.06; N-11.56. Calc. %: C-52.04; H-5.08; N-11.76.

Substitution of the appropriate N-cyano-formamidine derivatives and amino compounds for those of Example 6 and utilizing the procedure there described led to the production of the following formamidines:

(a) N-(2-hydroxy propyl)-N'-[4-(imidazol-4-yl)-phenyl]-formamidine
Maleate (ethanol), M.p. 140°–144° C. (dec.).
Analysis: $C_{21}H_{24}N_4O_9$: Found %: C-53.04; H-5.11; N-11.48. Calc. %: C-52.94; H-5.08; N-11.76.

(b) N-(2-Methylthio-ethyl)-N'-[4-(imidazol-4-yl)-phenyl]-formamidine
Maleate (ethanol 95%), M.p. 145°–146° C. (dec.).
Analysis: $C_{21}H_{24}N_4O_8S$: Found %: C-51.15; H-5.02; N-11.36 Calc. %: C-51.21; H-4.91; N-11.38.

(c) N-(2,2-Dimethoxy-ethyl)-N'-[4-(imidazol-4-yl)-phenyl]-formamidine
Maleate (ethanol), M.p. 143° C. (dec.).
Analysis: $C_{22}H_{26}N_4O_{10}$: Found %: C-52.01; H-5.38; N-10.96. Calc. %: C-52.17; H-5.18; N-11.06.

(d) N-(3-Methoxy-propyl)-N'-[4-imidazol-4-yl)-phenyl]-formamidine
Maleate (ethanol), M.p. 145°–146° C. (dec.).
Analysis: $C_{22}H_{26}N_4O_9$: Found %: C-53.61; H-5.16; N-11.22. Calc. %: C-53.87; H-5.34; N-11.42.

(e) N-(2-Ethylthio-ethyl)-N'-[4-(imidazol-4-yl)-phenyl]-formamidine
Hydrochloride (ethanol), M.p. 126°–129° C. (dec.).
Analysis: $C_{14}H_{20}Cl_2N_4S$: Found %: C-48.00; H-6.01; N-15.98. Calc. %: C-48.41; H-5.80; N-16.13.

(f) N-(3-Hydroxy-propyl)-N'-[4-(imidazol-4-yl)-phenyl]-formamidine
Maleate (ethanol), M.p. 138°–139° C. (dec.).
Analysis: $C_{21}H_{24}N_4O_9$ Found %: C-53.19; H-4.99; N-11.52. Calc. %: C-52.94; H-5.08; N-11.76.

(g) N-(1-Hydroxymethyl-propyl)-N'-[4-(imidazol-4-yl)-phenyl]-formamidine
Maleate (ethanol), M.p. 172°–173° C. (dec.).
Analysis: $C_{22}H_{26}N_4O_9$: Found %: C-54.02; H-5.30; N-11.51. Calc. %: C-53.87; H-5.34; N-11.42.

(h) N-[(2,2-Dimethyl-1,3-dioxolan-4-yl)-methyl]-N'-[4-(imidazol-4-yl)-phenyl]-formamidine
Maleate (ethanol), M.p. 179°–180° C. (dec.).
Analysis: $C_{24}H_{28}N_4O_{10}$: Found %: C-54.16; H-5.25; N-10.67. Calc. %: C-54.12; H-5.30; N-10.52.

(i) N-(3-N,N-Dimethylamino-propyl)-N'-[4-(imidazol-4-yl)-phenyl]-formamidine
Maleate (ethanol), M.p. 138°–139° C. (dec.).
Analysis: $C_{27}H_{33}N_5O_{12}$: Found %: C-51.91; H-5.33; N-11.09. Calc. %: C-52.34; H-5.37; N-11.30.

(j) N-(2-Cyano-ethyl)-N'-[4-(imidazol-4-yl)-phenyl]-formamidine
Maleate (ethanol), M.p. 140°–141° C. (dec.).
Analysis: $C_{21}H_{21}N_5O_8$: Found %: C-53.03; H-4.50; N-14.74. Calc. %: C-53.50; H-4.49; N-14.86.

(k) N-n-Butyl-N'-[4-(imidazol-4-yl)-2-methyl-phenyl]-formamidine
Fumarate (ethanol), M.p. 168°–170° C. (dec.).
Analysis: $C_{23}H_{28}N_4O_8$: Found %: C-56.70; H-6.00; N-11.49. Calc. %: C-56.55; H-5.78; N-11.47.

(l) N-Allyl-N'-[4-(imidazol-4-yl)-2-methyl-phenyl]-formamidine
Maleate (acetone), M.p. 148°–150° C. (dec.).
Found %: C-55.63; H-5.02; N-11.65. Calc. %: C-55.93; H-5.12; N-11.86.

(m) N-Propyl-N'-[2-methoxy-4-(imidazol-4-yl)-phenyl]-formamidine
Maleate (acetone), M.p. 165°–167° C. (dec.).
Analysis: $C_{22}H_{26}N_4O_9$: Found %: C-53.49; H-5.38; N-11.33. Calc. &: C-53.87; H-5.34; N-11.42.

(n) N-Ethyl-N'-[2-methoxy-4-(imidazol-4-yl)-phenyl]-formamidine
Maleate (acetone), M.p. 162° C. (dec.).
Analysis: $C_{21}H_{24}N_4O_9$: Found %: C-52.65; H-4.94; N-11.31. Calc. %: C-52.94; H-5.08; N-11.76.

(o) N-Methyl-N-isopropyl-N'-[4-(imidazol-4-yl)-phenyl]-formamidine
Hydrochloride (ethanol), M.p. 254°–255° C. (dec.).
Analysis: $C_{14}H_{20}Cl_2N_4$: Found %: C-53.20; H-6.44; N-17.55. Calc. %: C-53.33; H-6.39; N-17.77.

(p) N-Isopropyl-N'methyl-N'-[4-(imidazol-4-yl)-phenyl]-formamidine
Maleate (ethanol), M.p. 157°–158° C. (dec.).
Analysis: $C_{22}H_{26}N_4O_8$: Found %: C-55.23; H-5.49; N-11.62. Calc. %: C-55.69; H-5.52; N-11.81.

(q) N-n-Propyl-N'-methyl-N'-[4-(imidazol-4-yl)-phenyl]-formamidine
Maleate (acetone), M.p. 139°–140° C. (dec.).
Analysis: $C_{22}H_{26}N_4O_8$: Found %: C-55.47; H-5.39; N-11.75. Calc. %: C-55.69; H-5.52; N-11.81.

(r) N-Methyl-N'-[4-(imidazol-2-yl)-phenyl]-formamidine
Fumarate (ethanol), M.p. 195°–198° C. (dec.).
Analysis: $C_{34}H_{36}N_8O_{12}$: Found %: C-54.21; H-4.78; N-15.09. Calc. %: C-54.54; H-4.85; N-14.97.

(s) N-Isopropyl-N'-[4-(imidazol-2-yl)-phenyl]-formamidine
Fumarate (ethanol), M.p. 135°–140° C. (dec.).
Analysis: $C_{21}H_{24}N_4O_8$: Found %: C-55.78; H-5.38; N-12.25. Calc. %: C-54.77; H-5.25; N-12.17.

Example 7

N-sec.Butyl-N'-[4-(imidazol-2-yl)-phenyl]-formamidine

N-cyano-N'-[4-(imidazol-2-yl)-phenyl]-formamidine (3 g) was allowed to react with a 35% butylamine solution in water (7 ml). After 5 minutes of stirring, water (60 ml) was added to the solution and the oil which separated out was taken up in ethyl acetate. This solution was washed with water, dried and evaporated to dryness to give 3.3 g of the title compound as a thick oil. The base was purified via its fumarate in ethyl acetate solution. M.p. 125°–126° C.

Analysis: $C_{19}H_{22}N_4O_4$: Found %: C-61.14; H-6.01; N-14.92. Calc. %: C-61.61; H-5.99; N-15.13.

The following compounds were prepared in analogous manner:

(a) N-Allyl-N'-[3-(imidazol-2-yl)-phenyl]-formamidine
Maleate (ethanol), M.p. 170°–171° C. (dec.).
Analysis: $C_{21}H_{22}N_4O_8$: Found %: C-55.27; H-4.70; N-12.45. Calc. %: C-55.02; H-4.84; N-12.22.

(b) N-n-Propyl-N'-[3-(imidazol-2-yl)-phenyl]-formamidine
Maleate (ethanol), M.p. 172°–173° C. (dec.).
Analysis: $C_{21}H_{24}N_4O_8$; Found %: C-54.87; H-5.30; N-12.31. Calc. %: C-54.78; H-5.25; N-12.17.

EXAMPLE 8

N-[(4-Hydroxymethyl-1,3-dioxolan-2-yl)-methyl]-N'-[4-imidazol-4-yl)-phenyl]-formamidine A suspension of N-cyano-N'-[4-(imidazol-4-yl)-phenyl]-formamidine (1.17 g) and 4-hydroxymethyl-2-aminomethyl-1,3-dioxolane (3.7 g) in ethanol (25 ml) and water (0.3 ml) was stirred until a clear solution resulted. Ethanol (20 ml) was added, and the solution was filtered through charcoal. A solution of maleic acid (3.8 g) in ethanol was slowly added. The solid which crystallized out was filtered off and dried to give 1.9 g of the title compound.

Maleate (ethanol), M.p. 139°–141° C. (dec.).
Analysis: $C_{23}H_{26}N_4O_{11}$: Found %: C-51.96; H-4.94; N-10.39. Calc. %: C-51.68; H-4.90; N-10.48.

By using the appropriate N-cyano-formamidine derivatives and amines the following compounds were also prepared:

(a) N-(1-Methyl-2-hydroxyethyl)-N'-[4-(imidazol-4-yl)-phenyl]-formamidine
Maleate (acetone), M.p. 160° C. (dec.).
Analysis: $C_{21}H_{24}N_4O_9$: Found %: C-53.06; H-5.12; N-11.72. Calc. %: C-52.94; H-5.08; N-11.76.

(b) N-(2-Ethoxymethylthio-ethyl)-N'-[4-(imidazol-4-yl)-phenyl]-formamidine
Maleate (acetone), M.p. 139°–140° C. (dec.).
Analysis: $C_{23}H_{28}N_4O_9S$: Found %: C-51.40; H-5.25; N-10.43. Calc. %: C-51.48; H-5.26; N-10.44.

(c) N-n-Propyl-N'-[2-bromo-4-(imidazol-4-yl)-phenyl]-formamidine
Maleate (acetone), M.p. 162°–163° C.
Analysis: $C_{21}H_{23}BrN_4O_8$: Found %: C-47.08; H-4.27; N-10.35. Calc. %: C-46.76; H-4.29; N-10.39.

(d) N-Neopentyl-N'-[2-bromo-4-(imidazol-4-yl)-phenyl]-formamidine
Maleate (acetone), M.p. 151°–154° C.
Analysis: $C_{23}H_{27}BrN_4O_8$: Found %: C-48.06; H-4.73; N-9.69. Calc. %: C-48.68; H-4.79; N-9.87.

(e) N-(2-Methylthio-ethyl)-N'-[2-bromo-4-(imidazol-4-yl)-phenyl]-formamidine
Maleate (acetone), M.p. 150°–153° C. (dec.).
Analysis: $C_{21}H_{23}BrN_4O_8S$:
Found %: C-44.36; H-4.15; N-9.81. Calc. %: C-44.14; H-4.06; N-9.81.

(f) N-Neopentyl-N'-[2-chloro-4-(imidazol-4-yl)-phenyl]-formamidine
Maleate (acetone), M.p. 180°–181° C.
Analysis: $C_{23}H_{27}ClN_4O_8$: Found %: C-52.47; H-5.28; N-10.61. Calc. %: C-52.82; H-5.20; N-10.71.

(g) N-n-Propyl-N'-[2,6-dichloro-4-(imidazol-4-yl)-phenyl]-formamidine
Maleate (acetone), M.p. 143°–145° C. (dec.).

Analysis: $C_{21}H_{22}Cl_2N_4O_8$: Found %: C-47.73; H-4.09; N-10.65. Calc. %: C-47.65; H-4.19; N-10.58.

(h) N-Allyl-N'-[2-chloro-6-bromo-4-(imidazol-4-yl)-phenyl]-formamidine

Maleate (acetone), M.p. 148°–151° C. (dec.).

Analysis: $C_{21}H_{20}BrClN_4O_8$: Found %: C-43.98; H-3.64; N-9.69. Calc. %: C-44.11; H-3.52; N-9.80.

The compounds embraced by formula I above and their non-toxic, pharmacologically acceptable acid addition salts have useful pharmacodynamic properties. More particularly, they exhibit antiulcerogenic and gastric acid secretion inhibiting activities in warm-blooded animals such as rats.

The antagonistic activity of the compounds of the invention on histamine $H_2$-receptors is demonstrated either in vitro or in vivo by their inhibition of the $H_2$-dependent biological effects, which include the histamine-evoked positive chronotropic effect and the histamine-induced gastric secretion of acid respectively.

The inhibition of the positive chronotropic effect was investigated on isolated guinea pig atria suspended in an organ bath (50 ml) containing an oxygenated ($O_2$: 95%-$CO_2$: 5%) Krebs-Henseleit solution (pH 7.4) maintained at 32° C. The myocardial preparation, loaded with 1 g isometric tension, was allowed to stabilize 60 minutes, and myocardial contractions were recorded through an isometric lever connected to a strain-gauge coupler and the instantaneous rate was monitored with a cardiotachometer, and a heatwriting pen recorder. After two control responses to histamine ($10^{-6}$ g.ml$^{-1}$) the test compound was added to the bath at the desired final concentration and left for 30 minutes before the atria were again challenged with histamine. The chronotropic response obtained in the presence of the antagonist was then compared to the control response to histamine, and the percent reduction of the histamine $H_2$-evoked response was calculated. The average effective concentration ($EC_{50}$) of the $H_2$-antagonists was also calculated by standard procedure according to Dr. Waud, Analysis of Dose-Response Curves, in "Methods in Pharmacology" vol. 3, Smooth muscle, Ed. Daniel E. E. Paton, M., Plenum Press, New York, (1975); Ash and Schild, Br. J. Pharmacol. Chemother. 27, 427–439, 1966. The following table shows the results which were obtained.

TABLE I

In vitro inhibitory activity in histamine induced tachycardia (guinea pig atria).

| Compound of Example | $EC_{50}10^{-7}$ M |
|---|---|
| 6 | 5.88 |
| 6 (a) | 12.7 |
| 6 (b) | 3.27 |
| 8 (b) | 3.20 |
| 6 (j) | 16.0 |
| 6 (k) | 3.09 |
| 6 (l) | 2.94 |
| 6 (m) | 6.00 |
| 8 (c) | 3.50 |
| CIMETIDINE | 34.0 |

The ability of the test compounds to inhibit histamine-induced gastric secretion of acid was investigated after intravenous or intraduodenal administration in stomach-perfused rats, according to Gosh and Schild (Br. J. Pharmacol. Chemother. 13, 54, 1958).

The preparation of the animals under general anesthesia (urethane, lg.kg$^{-1}$ i.p.) and constant temperature, was achieved by inserting and tying in place polyethylene tubes (PE 50) in the esophagus and in the pyloric-antral region. After the stomach was washed to remove residual of foods, continuous perfusion of the stomach was started with saline, 0.5 ml.min$^{-1}$ (37° C.), primed by a Jobling peristaltic pump. After 30 minutes of perfusion adaptation, the stomach perfusate was collected in 30 minute samples, and titrated for acid content, expressed as μEq of NaOH 1N. As control acid output became constant, intravenous perfusion of histamine (1 mg.kg$^{-1}$ hr$^{-1}$) was started and maintained throughout the experimental period. After the acid secretion had reached the steadily higher level, increasing doses of the test compound were injected intravenously in order to obtain dose-response functions. The $ED_{50}$ was then calculated by standard procedure.

The results are shown in the following table:

TABLE II

In vivo antisecretory activity in histamine-induced gastric secretion (stomach-perfused rat).

| Compound of Example | $ED_{50}$ mg · kg$^{-1}$ (i.v.)* |
|---|---|
| 6 | 0.050 |
| 6 (a) | 0.043 |
| 6 (b) | 0.022 |
| 8 (b) | 0.083 |
| 6 (j) | 0.046 |
| 6 (k) | 0.078 |
| 6 (l) | 0.090 |
| 6 (m) | 0.059 |
| 8 (c) | 0.117 |
| CIMETIDINE | 0.560 |

*The values of activity are expressed taking the compound as a base.

For pharmaceutical purposes the compounds of the present invention are administered to warm-blooded animals perorally or parenterally as active ingredients in customary pharmaceutical compositions, that is, compositions consisting essentially of an inert pharmaceutical carrier and an effective amount of the active ingredient, such as tablets, coated pills, capsules, wafers, solutions, suspensions, emulsions, syrups, suppositories and the like. An effective amount of the compounds according to the present invention is from 0.14 to 7.14 mgm/kg body weight, preferably 0.28 to 2.14 mgm/kg body weight.

The following examples illustrate a few pharmaceutical compositions comprising a compound of the present invention as an active ingredient and represent the best modes contemplated of using the invention. The parts are parts by weight unless otherwise specified.

Example 9

Tablets

The tablet composition is compounded from the following ingredients:

| | |
|---|---|
| N—(2-Methoxy-ethyl)-N'—[4-(imidazol-4-yl)-phenyl]-formamidine hydrochloride | 50 parts |
| Lactose | 217 parts |
| Corn starch | 30 parts |
| Magnesium stearate | 3 parts |
| Total | 300 parts |

Preparation

The active ingredient, the lactose and the corn starch are mixed and homogeneously moistened with water. After screening of the moist mass and drying in a tray driver, the mixture is again passed through a screen and magnesium stearate is added. Then, the mixture is compressed into tablets weighing 300 mg each. Each tablet contains 50 mg of the active ingredient.

Example 10

Capsules

The capsule filler composition is compounded from the following ingredients:

| | |
|---|---|
| N—(2-Hydroxy-propyl)-N'—[4-(imidazol-4-yl)-phenyl]-formamidine maleate | 50 parts |
| Corn starch | 170 parts |
| Magnesium stearate | 2 parts |
| Total | 222 parts |

Preparation

The active ingredient is mixed with the excipients, and the mixture is passed through a screen and homogeneously mixed in a suitable device. The resulting mixture is filled into hard gelatin capsules (222 mg per capsule); each capsule contains 50 mg of the active ingredient.

Example 11

Hypodermic solution

The solution is compounded from the following ingredients:

| | |
|---|---|
| N—(2-Methylthio-ethyl)-N'—[4-(imidazol-4-yl)-phenyl]-formamidine hydrochloride | 50 parts |
| Sterile water | 5000 parts by vol. |

Preparation

The active ingredient is dissolved in the water, and the resulting solution is filled into 5 cc-ampules under sterile conditions. Each ampule contains 50 mg of the active ingredient.

Any one of the other compounds embraced by formula I or a non-toxic, pharmaceutically acceptable acid addition salt thereof may be substituted for the particular active ingredient in Examples 9 through 11. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claim.

We claim:

1. A compound of the formula

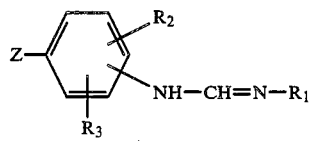

wherein
$R_1$ is straight or branched alkyl of 1 to 6 carbon atoms, hydroxy(alkyl of 1 to 4 carbon atoms), mono- or di-(alkoxy of 1 to 3 carbon atoms)(alkyl of 1 to 3 carbon atoms), (alkyl of 1 to 3 carbon atoms)thio(alkyl of 1 to 2 carbon atoms), (alkoxy of 1 to 2 carbon atoms)(alkyl of 1 to 3 carbon atoms)-thio(alkyl of 1 to 3 carbon atoms) or cyano(alkyl of 1 to 3 carbon atoms;
$R_2$ and $R_3$ are each independently hydrogen, alkoxy of 1 to 3 carbon atoms or halogen; and
Z is imidazol-2-yl or imidazol-4-yl;
provided, however, that when $R_1$ is straight or branched alkyl and $R_2$ and $R_3$ are hydrogen, Z is imidazol-2-yl; a tautomer thereof, or a non-toxic, pharmacologically acceptable acid addition salt thereof.

2. A compound of claim 1, where said acid addition salt is formed with maleic, hydrochloric, fumaric or sulfuric acid.

3. A compound of claim 1, where the formamidine radical is in the para-position on the benzene ring with respect to Z.

4. A compound of claim 3, where
$R_1$ is propyl, isopropyl, butyl, sec.butyl, isobutyl, neopentyl, methoxyethyl, dimethoxyethyl, hydroxypropyl, hydroxybutyl, methylthioethyl, ethylthioethyl, cyanoethyl or ethoxymethyl-thio-ethyl;
$R_2$ and $R_3$ are each independently hydrogen, methoxy, bromine, chlorine or fluorine; and
Z is imidazol-2-yl or imidazol-4-yl;
provided, however, that when $R_1$ is propyl, isopropyl, butyl, sec.butyl, isobutyl or neopentyl and $R_2$ and $R_3$ are hydrogen, Z is imidazol-2-yl; a tautomer thereof, or a non-toxic, pharmacologically acceptable acid addition salt thereof.

5. A compound of claim 1, which is N-(2-methoxyethyl)-N'-[4-(imidazol-4-yl)-phenyl]formamidine or a non-toxic, pharmacologically acceptable acid addition salt thereof.

6. A compound of claim 1, which is N-(2-hydroxypropyl)-N'-[4-(imidazol-4-yl)-phenyl]-formamidine or a non-toxic, pharmacologically acceptable acid addition salt thereof.

7. A compound of claim 1, which is N-(2-methyl-thioethyl)-N'-[4-(imidazol-4-yl)-phenyl]-formamidine or a non-toxic, pharmacologically acceptable acid addition salt thereof.

8. A compound of claim 1, which is N-(2-ethoxymethylthioethyl)-N'-[4-(imidazol-4-yl)-phenyl]-formamidine or a non-toxic, pharmacologically acceptable acid addition salt thereof.

9. A compound of claim 1, which is N-(2-cyanoethyl)-N'-[4-(imidazol-4-yl)-phenyl]-formamidine or a non-toxic, pharmacologically acceptable acid addition salt thereof.

10. A compound of claim 1, which is N-propyl-N'-[4-(imidazol-4-yl)-2-methoxy-phenyl]-formamidine or a non-toxic, pharmacologically acceptable acid addition salt thereof.

11. A compound of claim 1, which is N-propyl-N'-[4-(imidazol-4-yl)-2-bromo-phenyl]-formamidine or a non-toxic, pharmacologically acceptable acid addition salt thereof.

12. An antiulcerogenic and gastric acid secretion inhibiting pharmaceutical composition consisting essentially of an inert pharmaceutical carrier and an effective antiulcerogenic and gastric acid secretion inhibiting amount of a compound of claim 1.

13. The method of treating gastric ulcers and inhibiting gastric acid secretion in a warm-blooded animal in need thereof, which comprises perorally or parenterally administering to said animal an effective antiulcerogenic and gastric acid secretion inhibiting amount of a compound of claim 1.

* * * * *

UNITED STATES PATENT AND TRADEMARK OFFICE
CERTIFICATE OF CORRECTION

PATENT NO. : 4,666,932

DATED : May 19, 1987

INVENTOR(S) : ENZO CEREDA ET AL.

It is certified that error appears in the above-identified patent and that said Letters Patent is hereby corrected as shown below:

Column 6, line 23: "C-52.04" should read -- C-52.94 --.

Signed and Sealed this

Thirteenth Day of October, 1987

Attest:

DONALD J. QUIGG

Attesting Officer

Commissioner of Patents and Trademarks